(12) United States Patent
Islam et al.

(10) Patent No.: US 6,639,073 B2
(45) Date of Patent: Oct. 28, 2003

(54) RUTHENIUM COMPLEX USEFUL AS SENSITIZER, DYE-SENSITIZED OXIDE SEMICONDUCTOR ELECTRODE AND SOLAR CELL USING SAME

(75) Inventors: Ashraful Islam, Yamatotakada (JP); Hideki Sugihara, Tsukuba (JP); Kohjiro Hara, Tsukuba (JP); Masatoshi Yanagida, Tsukuba (JP); Hironori Arakawa, Tsukuba (JP)

(73) Assignee: National Institute of Advanced Industrial Science and Technology (JP)

( * ) Notice: Subject to any disclaimer, the term of this patent is extended or adjusted under 35 U.S.C. 154(b) by 16 days.

(21) Appl. No.: 10/087,218

(22) Filed: Mar. 4, 2002

(65) Prior Publication Data

US 2003/0144513 A1 Jul. 31, 2003

(51) Int. Cl.⁷ .................... C07F 15/00; H01L 31/0216; H01L 31/0224; H01G 9/20
(52) U.S. Cl. .................... 546/2; 556/137; 136/252; 136/256; 136/263; 257/40; 257/428; 257/431; 429/111
(58) Field of Search .................... 546/2; 556/137; 136/263, 252, 256; 257/40, 428, 431; 429/111

(56) References Cited

U.S. PATENT DOCUMENTS 6,278,056 B1 * 8/2001 Sugihara et al. ............ 136/263
2002/0170594 A1 * 11/2002 Arakawa et al. ............ 136/263

FOREIGN PATENT DOCUMENTS

EP          000975026 A2 *  1/2000
JP          2001-76776    *  3/2001

* cited by examiner

*Primary Examiner*—Porfirio Nazario-Gonzalez
(74) *Attorney, Agent, or Firm*—Lorusso, Loud & Kelly

(57) ABSTRACT

A ruthenium complex represented by the following formula:

$$RuL^1L^2X$$

wherein $L^1$ represents a 2,2';6',2"-terpyridine compound having at least one group selected from a carboxyl group, a salt of a carboxyl group, a sulfonic acid group, a salt of a sulfonic acid group, a phosphoric acid group and a salt of a phosphoric acid group, $L^2$ represents a diketonate ligand represented by the following formula:

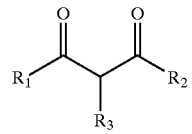

wherein $R_1$ and $R_2$ are independently selected from alkyl, alkoxyalkyl, aminoalkyl, perfluoroalkyl and aryl, $R_3$ represents a hydrogen atom, alkyl, alkoxyalkyl, aminoalkyl, perfluoroalkyl and aryl and X represents a monodentate ligand selected from a halide, a cyano group, a thiocyano group and a thiolate. A dye-sensitized oxide semiconductor electrode includes an electrically conductive body, an oxide semiconductor film provided on a surface of the electrically conductive body, and the above metal complex. A solar cell may be constructed from the above dye-sensitized oxide semiconductor electrode, a counter electrode, and a redox electrolyte contacting with both electrodes.

8 Claims, No Drawings

RUTHENIUM COMPLEX USEFUL AS SENSITIZER, DYE-SENSITIZED OXIDE SEMICONDUCTOR ELECTRODE AND SOLAR CELL USING SAME

TITLE OF THE INVENTION

Ruthenium Complex Useful as Sensitizer, Dye-Sensitized Oxide Semiconductor Electrode and Solar Cell Using Same

BACKGROUND OF THE INVENTION

This invention relates to a ruthenium complex having an organic ligand and to an electrode having a surface on which such a metal complex has been adsorbed. The present invention is also directed to a solar cell using such an electrode.

One known solar cell uses an oxide semiconductor electrode containing titanium oxide. It is also known to adsorb a sensitizing dye capable of absorbing a light of a visible region on such an electrode for the purpose of improving light energy absorbing efficiency thereof. The known sensitizing organic dye is, however, not fully satisfactory, because the wavelength region of light which can be absorbed by the dye is not sufficiently broad and because the coefficient of absorption of the dye is not high.

SUMMARY OF THE INVENTION

It is, therefore, the prime object of the present invention to provide a ruthenium complex which can efficiently absorb solar light of a long wave length region and which is useful as a sensitizer.

Another object of the present invention is to provide a dye-sensitized oxide semiconductor electrode using the above sensitizer.

It is a further object of the present invention to provide a solar cell using the above electrode, which has a high photoelectric conversion efficiency.

In accomplishing the foregoing objects, there is provided in accordance with the present invention a ruthenium complex represented by the following formula:

wherein
L$^1$ represents a 2,2'-6',2''-terpyridine compound having at least one group selected from the group consisting of a carboxyl group, a salt of a carboxyl group, a sulfonic acid group, a salt of a sulfonic acid group, a phosphoric acid group and a salt of a phosphoric acid group, L$^2$ represents a diketonate ligand represented by the following formula:

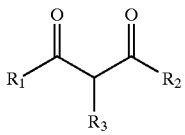

wherein R$_1$ and R$_2$ are independently selected from alkyl, alkoxyalkyl, aninoalkyl, perfluoroalkyl and aryl, R$_3$ represents a hydrogen atom, alkyl, alkoxyalkyl, aminoalkyl, perfluoroalkyl and aryl, and X represents a monodentate ligand selected from the group consisting of a halide (halogen), a cyano group, a thiocyano group and a thiolate.

In another aspect, the present invention provides a dye-sensitized oxide semiconductor electrode comprising an electrically conductive body, an oxide semiconductor film provided on a surface of said electrically conductive body, and the above ruthenium complex adsorbed on said film.

The present invention also provides a solar cell comprising the above dye-sensitized oxide semiconductor electrode, a counter electrode, and a redox electrolyte contacting with said dye-sensitized oxide semiconductor electrode and said counter electrode.

Other objects, features and advantages of the present invention will become apparent from the detailed description of the preferred embodiments of the invention to follow.

DETAILED DESCRIPTION OF THE PREFERRED EMBODIMENTS OF THE INVENTION

The novel ruthenium complex according to the present invention is represented by the following formula:

$$\text{RuL}^1\text{L}^2\text{X} \qquad (I)$$

wherein L$^1$ represents a 2,2';6',2''-terpyridine compound having at least one group selected from a carboxyl group, a sulfonic acid group, a phosphoric acid group and salts thereof. One typical 2,2';6',2'-terpyridine compound is represented by the following formula:

in which R is a carboxyl group (—COOH), a sulfonic acid group (—SO$_3$H), a phosphoric acid group (—PO$_4$H$_2$) or a salt thereof (—COOM, —SO$_3$M or —PO$_4$M) where M is an cation such as an ammonium ion, a substituted ammonium ion or a metal ion such as an alkali metal ion). The substituted or unsubstituted ammonium ion may be represented by the formula:

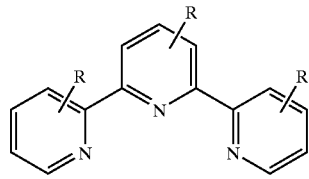

wherein R$^{11}$, R$^{12}$, R$^{13}$ and R$^{14}$ each stand for a hydrogen atom or an alkyl group which is preferably a lower alkyl group such as C1 to C4 alkyl group.

In the above formula (I), L$^2$ represents a diketonate ligand represented by the following formula:

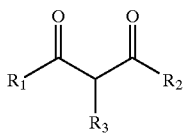

wherein R$^1$ and R$_2$ are independently selected from alkyl, alkoxyalkyl, aminoalkyl, perfluoroalkyl and aryl, R$_3$ represents a hydrogen atom, alkyl, alkoxyalkyl, aminoalkyl, perfluoroalkyl and aryl. The "alkyl, alkoxyalkyl, aminoalkyl and perfluoroalkyl" preferably have 1–30 carbon atoms.

In the above formula (I), X represents a monodentate to ligand selected from a halide, a cyano group (—CN), a thiocyano group (—SCN) and a thiolate (—SR') where R' is an organic group such as alkyl or aryl.

The above described ruthenium complex according to the present invention may be produced, for example, as follows.

A ruthenium complex of the formula $RuL^1Cl_3$ is first produced. For example, $RuCl_3$ and $L^1$ are first refluxed in a suitable solvent to form $RuL^1Cl_3$. This is then reacted with $L^2$ to obtain $RuL^1L^2Cl$. If desire, the resulting complex is further reacted with X to form $RuL^1L^2X$.

The ruthenium complex according to the present invention can efficiently absorb light of a wide wavelength and, hence, is suitably used as a sensitizing dye for the fabrication of a dye-sensitized oxide semiconductor electrode.

Such an electrode may be prepared by applying a dispersion or slurry containing fine powder of an oxide semiconductor on an electrically conducting substrate to form a semiconductor layer. A liquid containing the ruthenium complex is then applied to a surface of the semiconductor layer to adsorb the ruthenium complex thereon.

It is preferable that the oxide semiconductor have as small a diameter as possible. Generally the particle size of the oxide semiconductor particles is not greater than 5,000 nm, preferably not greater than 50 nm. The semiconductor particles generally has a specific surface area of at least 5 $m^2/g$, preferably at least 10 $m^2/g$. Any solvent may be used for dispersing the semiconductor particles therein. Water, an organic solvent or a mixture thereof may be used. Illustrative of suitable organic solvent are alcohols such as methanol and ethanol, ketones such as acetone, methyl ethyl ketone and acetyl acetone, and hydrocarbons such as hexane and cyclohexane. Additives such as a surfactant and a thickening agent (e.g. a polyhydric alcohol such as polyethylene glycol) may be added into the dispersion. The dispersion generally has a content of the oxide semiconductor particles in the range of 0.1–70% by weight, preferably 0.1–30% by weight.

Any conventionally used oxide semiconductor particles may be used for the purpose of the present invention. Examples of oxide semiconductors include oxides of transition metals such as Ti, Nb, Zn, Sn, Zr, Y, La and Ta and perovskite oxides such as $SrTiO_3$ and $CaTiO_3$.

The dispersion is applied onto a surface of a substrate. The coating is then dried and calcined in air or in an inert atmosphere to form a layer of the oxide semiconductor. Any known substrate may be suitably used for the purpose of the present invention. Thus, the substrate may be, for example, a refractory plate such as a glass plate on which an electrically conductive layer such as $In_2O_3$ or $SnO_2$ is laminated, or an electrically conductive metal plate. The thickness of the substrate is not specifically limited but is generally 0.3–5 mm. The laminate is generally transparent or translucent.

The coating of the oxide semiconductor particles, which is low in mechanical strength, is calcined to obtain a calcined or sintered layer having high mechanical strengths and high adhesion to the substrate. The calcination is performed at a temperature of generally not higher than 1,000° C., preferably 300–800° C., more preferably 500–800° C. The calcined layer is preferably porous in nature and preferably has a thickness of at least 10 nm, more preferably 100–10,000 nm, and a ratio of the actual surface area to the apparent surface area of at least 10, more preferably at least 100. The upper limit of the ratio is not specifically limited, but is generally 1,000–2,000. At least 100 of the ratio is preferred for reasons of an increased surface area of a layer of the metal complex formed thereon. The ratio of the actual surface area to the apparent surface area may be controlled by controlling the particle size and the specific area of the oxide semiconductor particles and by controlling the calcination temperature.

The apparent surface area of the calcined layer is intended to refer to an ordinary surface area. For example, when the layer has a rectangular parallelopiped shape, the apparent surface area is a product of the length and the width thereof. The actual surface area is a BET surface area determined by the measurement of an adsorption amount of a krypton gas at liquid nitrogen temperature using a BET surface measuring device (ASAP2000 manufactured by Micromeritex Inc.).

As described previously, a coating liquid containing the ruthenium complex according to the present invention is applied onto a surface of the calcined semiconductor layer to adsorb the ruthenium complex on a surface of the semiconductor layer. The adsorbed ruthenium complex layer is preferably a monomolecular layer. The adsorption may be performed by immersing the substrate having the oxide semiconductor layer in a solution of the ruthenium complex in an organic solvent.

For the purpose of improving the adsorption efficiency of the ruthenium complex, it is desirable to previously remove air bubbles contained in the semiconductor layer by placing the substrate in a reduced pressure environment and/or heating the substrate. The immersion of the substrate is generally performed for 30 minutes to 24 hours. The immersion may be repeated, if necessary. The semiconductor layer on which the sensitizing dye has been adsorbed is then dried at room temperature to about 80° C.

If desired, two or more kinds of sensitizing dyes may be used in combination to broaden a range of wavelengths of light which is absorbed by the dye-sensitized semiconductor layer. To adsorb a plurality of sensitizing dyes, a common solution containing all sensitizing dyes can be used. Alternatively, a plurality of solutions containing respective dyes can be used.

Any solvent may be used for dissolving the sensitizing dye. Illustrative of suitable solvents are methanol, ethanol, acetonitrile, dimethylformamide and dioxane. The concentration of the dye solution is suitably determined according to the kind of the dye. The sensitizing dye is generally dissolved in the solvent in an amount of 1–10,000 mg, preferably 10–500 mg, per 100 ml of the solvent.

The dye-sensitized oxide semiconductor thus obtained is advantageously used as an electrode for a solar cell. In addition to the above dye-sensitized oxide semiconductor electrode, the solar cell generally has a counter electrode, and a redox electrolyte through which both electrodes contact with each other.

The redox electrolyte may be, for example, $I^-/I_3^-$ system, $Br^-/Br_3^-$ system and quinone/hydroquinone system. Such a redox electrolyte system may be prepared by any known method. For example, The $I^-/I_3^-$ type redox electrolyte may be prepared by mixing ammonium iodide with iodine. The electrolyte may be liquid or solid. The solid electrolyte is obtained by dispersing the electrolyte in a polymeric material. In the case of a liquid electrolyte, an electrochemically inert solvent such as acetonitrile, propylene carbonate or ethylene carbonate may be used.

Any electrically conductive material may be used as the counter electrode. Illustrative of suitable counter electrodes are a platinum electrode, a platinum coated conductor electrode, a rhodium electrode, a ruthenium electrode and a carbon electrode.

The two electrodes and electrolyte are accommodated in a case or encapsulated with a resin, in such a state that the dye-sensitized oxide semiconductor electrode is capable of being irradiated with a light. When the semiconductor electrode is irradiated with a light such as Aft solar beam, an electric current flows therebetween because of an electric potential difference therebetween.

The following examples will further illustrate the present invention.

EXAMPLE 1

Ruthenium trichloride and 4,4',4"-trimethoxycarbonyl-2,2';2",6-terpyridine were refluxed in an ethanol-methylene chloride mixed solvent for 2 hours. The reaction mixture was then cooled to room temperature and trichloro(4,4',4"-trimethoxycarbonyl-2,2';2",6-terpyridine)Ru(II) in the form of precipitates was collected by filtration. This was dissolved in methanol and reacted with 2 equivalents of acetylacetone in the presence of triethylamine under reflux. The solvent was then removed in vacuo from the reaction mixture to obtain acetylacetonatechloro(4,4',4"-tricarboxy-2,2';2",6-terpyridine)Ru(II). This was mixed with 3 equivalents of sodium thiocyanate in dimethylformamide and with triethylamine with heating. This was further mixed with triethylamine and the resulting mixture was reacted under reflux for 12 hours. The solvent was then removed in vacuo to leave solids. The solids were dissolved in water and acidified with hydrochloric acid to form precipitates. The precipitates were collected by filtration and dried to obtain acetylacetonatethiocyanate (4,4',4"-tricarboxy-2,2',2",6-terpyridine)ruthenium(II) (a compound of the formula (I) in which $L^1$ represents 4,4',4"-tricarboxy-2,2';2",6-terpyridine, $L^2$ represents acetylacetonate and X represents thiocyanate).

EXAMPLE 2

Example 1 was repeated in the same manner as described except that 2,4-diketo-1-trifluoropentane was substituted for acetylacetone to obtain trifluoroacetylacetonate-thiocyanate (4,4',4"-tricarboxy-2,2';2",6-terpyridine)ruthenium(II) (a compound of the formula (I) in which $L^1$ represents 4,4',4"-tricarboxy-2,2';2",6-terpyridine, $L^2$ represents trifluoroacetylacetonate and X represents thiocyanate).

EXAMPLE 3

Example 1 was repeated in the same manner as described except that 2,4-diketo-1-trifluorooctane was substituted for acetylacetone to obtain trifluoroacetylmethylhexylketonate-thiocyanate (4,4',4"-tricarboxy-2,2';2",6-terpyridine)ruthenium(II) (a compound of the formula (I) in which $L^1$ represents 4,4',4"-tricarboxy-2,2';2",6-terpyridine, $L^2$ represents trifluoroacetylmethylhexylketonate and X represents thiocyanate).

EXAMPLE 4

A titanium oxide semiconductor film-bearing glass substrate was immersed in each of solutions of the ruthenium complexes obtained in Examples 1–3 dissolved in ethanol at 80° C. under reflux. Each of the treated substrates was then dried at room temperature to obtain a dye-sensitized oxide semiconductor electrode. A cell was constructed using each semiconductor electrode and a counter electrode which was an electrically conductive glass having deposits of a Pt layer. The two electrodes were spaced apart from each other to define a gap in which a redox electrolyte was placed.

Each of the thus constructed cells was irradiated with a simulated solar beam of AM 1.5. Short-cut current, release voltage and FF (fill factor) of each cell are shown in Table 1.

TABLE 1

| Example No. | Short-cut current (mA/cm$^2$) | Release voltage (V) | FF (%) |
|---|---|---|---|
| 1 | 10.6 | 0.59 | 66 |
| 2 | 18.3 | 0.63 | 68 |
| 3 | 16.0 | 0.63 | 67 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A ruthenium complex represented by the following formula:

$$RuL^1L^2X$$

wherein
$L^1$ represents a 2,2';6',2"-terpyridine compound having at least one group selected from the group consisting of a carboxyl group, a salt of a carboxyl group, a sulfonic acid group, a salt of a sulfonic acid group, a phosphoric acid group and a salt of a phosphoric acid group, $L^2$ represents a diketonate ligand represented by the following formula:

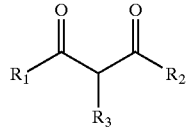

wherein $R_1$ and $R_2$ are independently selected from alkyl, alkoxyalkyl, aminoalkyl, perfluoroalkyl and aryl, $R_3$ represents a hydrogen atom, alkyl, alkoxyalkyl, aminoalkyl, perfluoroalkyl and aryl, and X represents a monodentate ligand selected from the group consisting of a halide, a cyano group, a thiocyano group and a thiolate.

2. A ruthenium complex as claimed in claim 1, wherein $R_1$ represents a perfluoroalkyl group having 1–7 carbon atoms, $R_2$ represents an alkyl group having 1–30 carbon atoms, an alkoxyalkyl group having 1–30 carbon atoms, an aminoalkyl group having 1–30 carbon atoms or an aryl group, and $R_3$ represents a hydrogen atom.

3. A ruthenium (II) complex as claimed in claim 1, wherein $L^1$ represents 4,4',4"-tricarboxy-2,2';2",6-terpyridine, $L^2$ represents acetylacetonate and X represents thiocyanate.

4. A ruthenium complex (II) as claimed in claim 1, wherein $L^1$ represents 4,4',4"-tricarboxy-2,2';2",6-terpyridine, $L^2$ represents trifluoroacetylacetonate and X represents thiocyanate.

5. A ruthenium complex (II) as claimed in claim 1, wherein $L^1$ represents 4,4',4"-tricarboxy-2,2';2",6-terpyridine, $L^2$ represents trifluoroacetylmethylhexylketonate and X represents thiocyanate.

6. A ruthenium complex (II) as claimed in claim 1, wherein $L^1$ represents 4,4',4$^1$-tricarboxy-2,2';2",6-terpyridine, $L^2$ represents acetylacetonate and X represents chlorine.

7. A dye-sensitized oxide semiconductor electrode comprising an electrically conductive body, an oxide semiconductor film provided on a surface of said electrically conductive body, and a metal complex according to claim 1 adsorbed on said film.

8. A solar cell comprising a dye-sensitized oxide semiconductor electrode according to claim 7, a counter electrode, and a redox electrolyte contacting with said dye-sensitized oxide semiconductor electrode and said counter electrode.

* * * * *

UNITED STATES PATENT AND TRADEMARK OFFICE
CERTIFICATE OF CORRECTION

PATENT NO. : 6,639,073 B2
DATED : October 28, 2003
INVENTOR(S) : Islam et al.

It is certified that error appears in the above-identified patent and that said Letters Patent is hereby corrected as shown below:

Column 2,
Line 62, delete "to".

Column 4,
Line 63, delete "Aft".

Column 6,
Line 65, "4,4',4'"" should read -- 4,4',4" --.

Signed and Sealed this

Twelfth Day of October, 2004

JON W. DUDAS
*Director of the United States Patent and Trademark Office*